Figure 1:
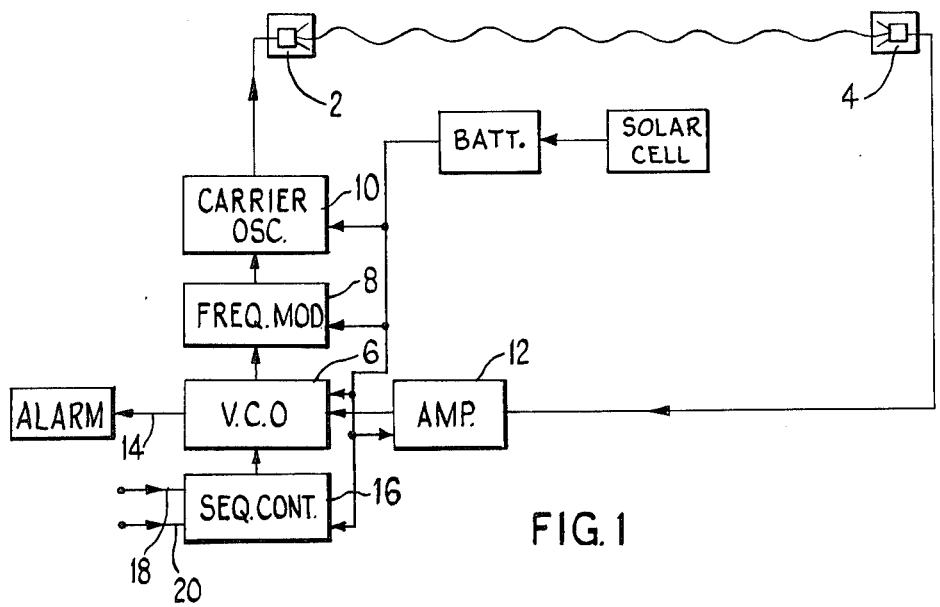

United States Patent [19]

Redding

[11] 4,119,950

[45] Oct. 10, 1978

[54] GAS DETECTION

[76] Inventor: Robert J. Redding, September House, Cox Green La., Maidenhead, Berkshire, England, SL6 3EL

[21] Appl. No.: 770,112

[22] Filed: Feb. 18, 1977

[30] Foreign Application Priority Data

Apr. 7, 1976 [GB] United Kingdom ............... 14179/76

[51] Int. Cl.² ...................... G08B 21/00; G01N 29/02
[52] U.S. Cl. ........................................ 340/524; 73/24; 340/539; 340/632
[58] Field of Search ...................... 73/24, 23, 71.5 US; 324/83 FE; 340/213 Q, 223, 237 R, 261, 384 E; 325/363, 364

[56] References Cited

U.S. PATENT DOCUMENTS

| 3,047,815 | 7/1962 | Boose | 324/83 FE |
| 3,120,750 | 2/1964 | Root | 73/24 |
| 3,199,037 | 8/1965 | Graves | 324/83 FE |
| 3,427,481 | 2/1969 | Lenahan et al. | 73/71.5 US |
| 3,449,748 | 6/1969 | Thyssens | 324/83 FE |
| 3,613,092 | 10/1971 | Schumann et al. | 340/213 Q |
| 3,624,626 | 11/1971 | MacCreadie | 340/223 |
| 3,789,655 | 2/1974 | Passeri | 73/24 |
| 3,828,607 | 8/1974 | Janzen et al. | 73/23 |

Primary Examiner—Stephen A. Kreitman
Attorney, Agent, or Firm—Kemon & Estabrook

[57] ABSTRACT

Apparatus for monitoring gas content on a site, to provide an indication if an undesirable gas content occurs, comprises a transmitter for feeding ultrasonic waves through the gas to a receiver. The ultrasonic waves are frequency-modulated and the phase of the modulation at the receiver relative to that at the transmitter is monitored. Either the relative phase is maintained constant, for example by a phase-locked loop so that the modulation frequency varies as a function of the gas content, or the frequency is maintained constant and the phase varies with the gas content. Any appreciable change in the frequency or phase may indicate a potentially undesirable change in the gas content. A plurality of transmitter/receiver pairs can be enabled in sequence to monitor a large area, the respective frequencies or phase displacements being monitored by a central processor.

15 Claims, 6 Drawing Figures

U.S. Patent Oct. 10, 1978 Sheet 2 of 2 4,119,950
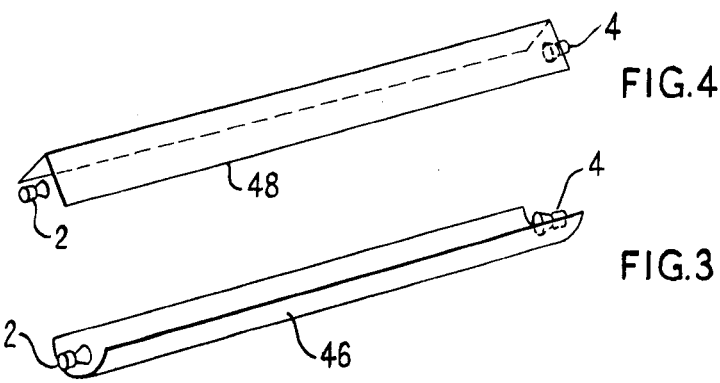
FIG.4
FIG.3
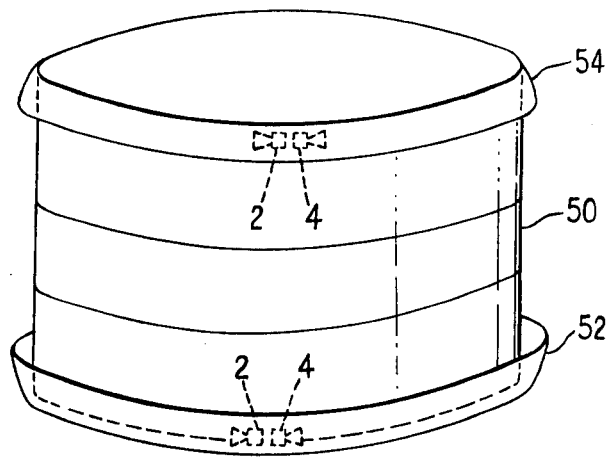
FIG.5
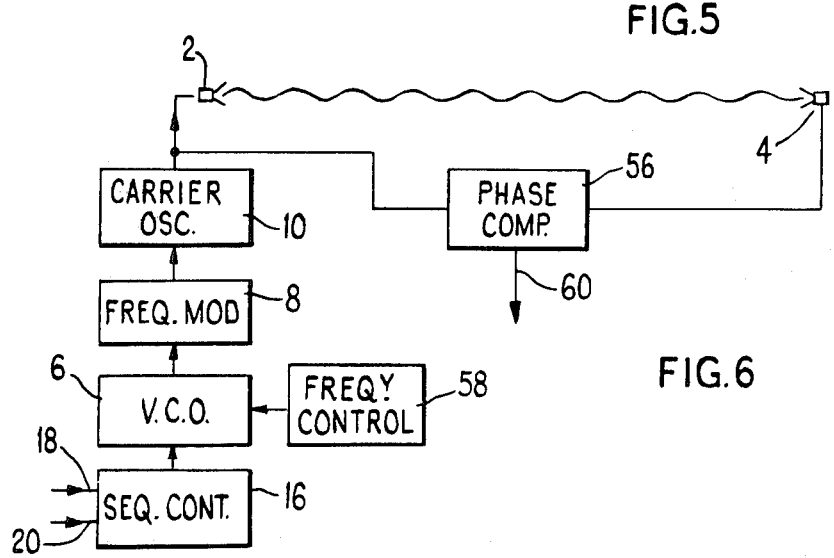
FIG.6

GAS DETECTION

This invention relates to the monitoring of gas content in atmospheres, particularly in hazardous situations.

There are many situations, such as in chemical plant and oil rigs, where it is desirable to monitor the concentration of gases, particularly flammable gases, in the atmosphere and to give an alarm when the concentration becomes excessive, or when there is an abnormal change in concentration, so that action can be taken to avoid a fire and/or an explosion, or to avoid a health hazard to personnel, or to evacuate the site if avoiding action cannot be taken.

The gas detectors at present in use suffer from a number of disadvantages. Firstly they are able to check the gas content only by taking small samples at spot points, and cannot, therefore, monitor the concentration rapidly and accurately over an area.

Furthermore, the known gas detectors are generally hot-wire instruments which require an appreciable amount of power to preheat them. In a large installation, such as an oil rig, several kilowatts of power might be needed merely to feed these detectors and the associated electronics. The presence of the hot wire can, in itself, constitute a hazard, since it could act as an igniter if an excessive gas concentration were to occur. In fact, it is often recommended that such detectors be switched off if build-up of the gas concentration to an explosive level is threatened.

It is an object of the present invention to provide apparatus and a system for monitoring gas content in a manner which does not result in appreciable production of heat, and is intrinsically safe.

The invention also allows checking of the gas content over an extended area in a single operation, as compared with the conventional methods which would require many spot checks at different points to be made in order to cover a corresponding area.

According to the invention, apparatus for monitoring gas content in a space comprises means for generating an audio-frequency electric signal; means for generating a carrier electric signal; a frequency modulator for modulating the frequency of the carrier signal in accordance with the audio-frequency signal; a first transducer energisable by the frequency modulated carrier signal to transmit ultrasonic energy along a path through the gas; a second transducer for receiving at least part of the ultrasonic energy after transmission along said path and for producing an output electric signal in response thereto; and means for monitoring the phase relation between the audio modulation received at the second transducer and that transmitted by the first transducer, to give an indication of the gas content.

Figure 2:
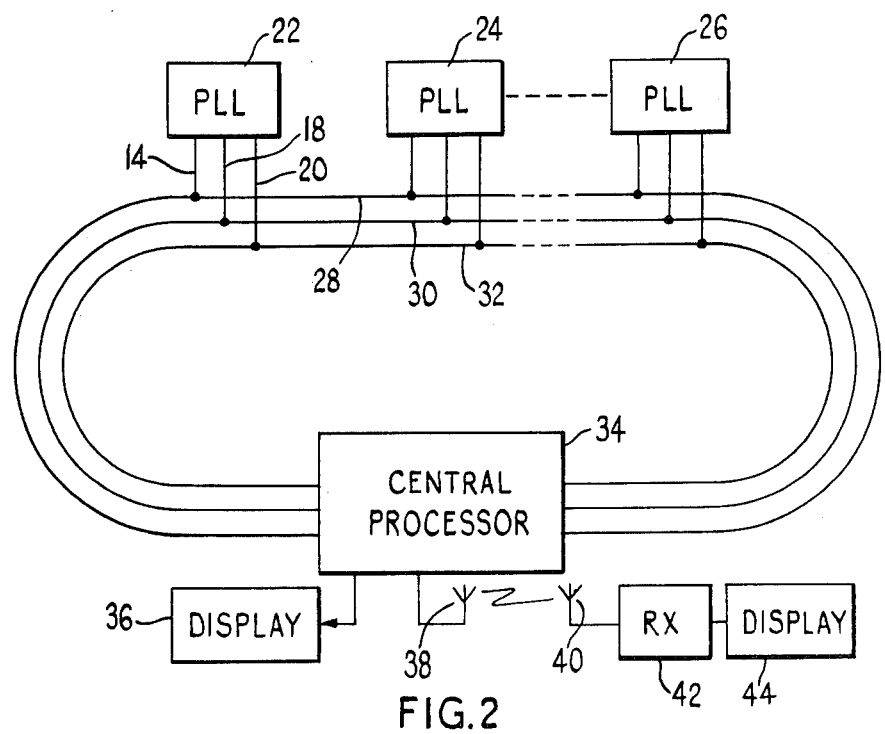

Embodiments of the invention will now be described, by way of example, with reference to the accompanying drawings, in which:

FIG. 1 is a block schematic diagram of a gas content monitoring apparatus in accordance with the invention, FIG. 2 is a block schematic diagram showing a monitoring system comprising a number of such apparatuses interconnected to operate sequentially and to report back to a control station, FIGS. 3 and 4 are pictorial views of accessories for use with the apparatus of FIG. 1, FIG. 5 is a pictorial view of a cylindrical tank provided with apparatus for detecting leaks from the tank, and FIG. 6 is a block schematic diagram of a second gas content monitoring apparatus in accordance with the invention.

Referring to FIG. 1 of the drawings, ultrasonic transducers 2 and 4 act as a transmitter and a receiver, respectively, of ultrasonic waves. The transducers are so located that the ultrasonic waves pass through an area in which the gas content is to be monitored.

An audio frequency signal is generated by a voltage-controlled oscillator 6 and is fed to a modulator 8 which frequency modulates, in accordance with the audio-frequency signal, a carrier signal generated by a carrier frequency oscillator 10. The carrier frequency may conveniently be maintained at 40 kHz for a transducer spacing of 0.5 to 15 meters.

The output of the receiving transducer 4 is fed, via an amplifier 12, to the oscillator 6, so that the oscillator 6 is contained in a closed phase-locked loop including the path through the gas.

The phase-locked loop maintains a zero phase difference between the audio modulation at the receiving transducer 4 and that at the transmitting transducer 2. The frequency of oscillation of the oscillator 6 is determined by the speed of propagation of the ultrasonic waves through the gas, and so is dependent upon the gas content. A line 14 from the oscillator 6 carries a signal from the oscillator, representative of the frequency of the audio-frequency oscillation.

A sequence control unit 16 is provided to switch the oscillator 6 on and off in response to the application thereto of a d.c. supply on lines 18 and 20. This allows for sequential control of a number of phase-locked loops such as will be described later with reference to FIG. 2 of the drawings.

The speed of sound varies greatly in dependence upon the gas through which it passes. Thus, for example, the speed of sound in air is 331 meters per second, whereas in methane it is 430 meters per second, and in hydrogen it is 1286 meters per second. Hence, if a space which is air-filled is being monitored, a certain modulation frequency will be maintained in the loop, with only insignificant, if any, changes in frequency. If, then, a foreign gas such as methane leaks into the space or otherwise becomes present therein, the modulation frequency will change accordingly, and this change can be made to operate an alarm and/or a display if the change exceeds a predetermined limit.

The transducers 2 and 4 may be a conventional loudspeaker and microphone, respectively, or they may, for example, be ceramic or piezo-electric devices. These devices may be fully encapsulated and may be of cheap nonrepairable construction, and are preferably provided with simple means for attachment of the devices to the steel work of the plant. Simple plug and socket connections to the supply and information lines are preferably provided.

The speed of sound in a gas is affected by the temperature of the gas. For example, air has a temperature coefficient of speed of +0.607 meter per second per degree Centigrade. This provides a facility for monitoring changes in temperature, since the frequency of oscillation in the phase-locked loop will change with the temperature of a given atmospheric composition. Humidity will also have an effect on the frequency, but changes in pressure of the atmosphere will have little effect.

The whole area, or selected parts of the area, of a chemical plant, an oil rig, or other site where a hazardous atmosphere could be present, could be monitored by a network of transmitter/receiver loops as described above, each monitoring its respective ultrasonic wave path.

Under normal operating conditions, the oscillation frequency of all of the transmitter/receiver pairs located in the normal ambient air of the site will be substantially the same, but the actual value of this frequency may wander slightly as a result of changes in ambient temperature and/or humidity. If necessary, temperature and humidity sensors may be used to provide signals for compensating the audio frequency for such changes.

In the event of a change in the gas content of the atmosphere at any monitored part of the site due, for example, to leakage of gas or the abnormal combustion of materials, the apparatus monitoring that part will suffer an abnormal change in audio modulation frequency.

A pattern of modulation frequencies will be set up for the site and, in general, the actual frequency values will not be of any special significance. Any deviation from the pattern will, however, be noted and watched, and the onset of any potentially dangerous situation will be apparent. Thus, a substantial change in frequency of one or more adjacent loops might indicate a local leakage of gas, or a local increase in temperature brought about by, for example, a blocked vent or silencer.

A high-pressure leak, such as a steam leak, might itself produce ultrasonic waves impinging on one or more receivers and thereby producing spurious changes in the normal frequency pattern.

In order to minimise the power required to operate the system including a network of transmitter/receiver pairs, the pairs can be energised in sequence, either in their respective self-contained loops, or with the pairs connected in sequence into a single electronic circuit (voltage-controlled oscillator, etc). The monitored area can be completely scanned over a relatively short period taking, say, one second for the loop to stabilise for each pair and to indicate its oscillation frequency. Hence, if 180 transmitter/receiver pairs were in use on a site, the whole area could be monitored every three minutes.

The modulation frequency value for each transmitter/receiver pair can be stored during each scanning period, and during a scan the new frequency value can be compared with the corresponding value for the previous scan, and significant changes can be indicated automatically and, if necessary, an alarm initiated. An indication can be obtained as to whether the danger is increasing or decreasing, and also as to whether the danger is spreading and in which direction.

If necessary, other instruments can be brought into operation, either automatically or by an operator, to give an accurate measurement of the gas concentration or an analysis of the gas content, or to give any other accurate assessment of the problem.

A minicomputer or a microprocessor could be used for indicating when a significant deviation in frequency has occurred. Such a computer or processor could store data relating to expected events or cyclic variations, and could look up such data before initiating an alarm.

Thus, the breaking or attenuation of one or more wave paths by the presence of a service man could be ignored by the computer or processor logic. If the monitored site is unmanned, the safe progress of a visiting service man around the site could be mentioned remotely.

A simple system in which a number of transmitter/receiver pairs are connected sequentially to a central processor is shown schematically in FIG. 2 of the drawings. This system comprises circuits, of which only three (22, 24 and 26) are shown for the sake of example, each comprising a complete phase-locked loop as shown in FIG. 1. The lines 14, 18 and 20 of each circuit are joined to respective lines 28, 30 and 32 of a three-wire ring which links the circuits to the central processor 34.

The processor 34 energises each of the circuits 22, 24 etc. in turn by successive switchings on and off of the d.c. supply on the lines 30 and 32. This may be achieved by making each such circuit turn on only after a predetermined numer of d.c. switchings have occurred, e.g. the circuits 22, 24 and 26 in FIG. 2 will turn on only every third time that the d.c. supply comes on, the initial turning on of the circuits being staggered to give sequential operation.

The processor 34 also receives, over the lines 14 and 28, an indication of the modulation frequency from each circuit in turn. This indication is stored and is compared with previous frequency indications for the same circuit and any stored data relating to expected events etc., as mentioned above, are taken into account.

If a significant change in frequency from any of the circuits 22, 24 and 26 is detected, the processor 34 feeds an output to a display unit 36 and/or produces a corresponding radio-frequency output which is fed to a transmitting aerial 38 for reception at a remote receiving station comprising an aerial 40, a receiver 42 and a display unit 44.

The display units 36 and 44 may comprise maps or 3-dimensional models of the site, with lights, such as light emitting diodes, situated at positions corresponding to the siting of the respective transmitter/receiver pairs in the plant. Such a display would give a very speedy warning of a hazardous condition and would indicate the exact area of the plant involved.

The transmitter/receiver pairs might be disposed over the area of the plant along the sides of a rectangle to form a "grid" pattern of ultrasonic waves over the area. The lights could then be sited at the intersections of a corresponding grid pattern on the model.

In a large plant the transmitter/receiver pairs might be divided into groups (e.g. 12 pairs per group), each group having a separate connection back to its own section of the processor. The groups might be interleaved over the monitored area, so that transmitter/receiver pairs from different groups monitor adjacent elements of the area. This would provide some redundancy in the event of failures, and hence substantially increase the reliability of the system.

Clearly, the length of any particular ultrasonic wave path will determine the sensitivity of that path to a gas leak. Detection of the position of a leak along the length of the path might be determined, if necessary, by a "successive halving" timing method using auxiliary transducers sited at $\frac{1}{4}$, $\frac{1}{2}$ and $\frac{3}{4}$ of the distance between the main transducers.

Any movement of the atmosphere, for example in windy conditions, might change the frequencies of several adjacent loops, but comparison of the frequencies, particularly over a number of successive scans, could avoid masking of the presence of a hazard. Extending this further, monitoring of the presence of foreign gas in a duct through which air is flowing could be achieved. In this case, Doppler shift in frequency could provide useful information as to the rate of flow of the air.

On the other hand, greater accuracy in the monitoring of atmospheres can be achieved if air currents are avoided or reduced. FIGS. 3 and 4 show means for reducing such currents in the region of the ultrasonic waves between the transmitter/receiver pairs. In FIG. 3 a trough-like member 46 is positioned immediately beneath the path of the ultrasonic waves between the transmitter 2 and the receiver 4. The member 46 provides some protection from the above-mentioned air currents, and also tends to accumulate any foreign gas (e.g. pentane) which is heavier than air, so that the presence of the gas is more easily detected. The transmitter 2 and the receiver 4 will preferably be mounted near the floor of the site.

If, on the other hand, an inverted trough-like member 48 (FIG. 4) is positioned above the wavepath, it will accumulate gases (e.g. methane) which are lighter than air. In this case, the receiver and transmitter are mounted at a high level on the site.

In the FIG. 3 and FIG. 4 arrangements, the trough-like members could be of any suitable shape in which the top or bottom (as the case may be) is sufficiently open to allow the ingress of the gases.

If there is a low ambient level of foreign gas leaking into the atmosphere, the oscillation frequency will stabilise and the presence of the gas can be ignored. However, if an increase in the leakage occurs, the monitoring apparatus will give an early warning of the change in conditions.

Two adjacent trough-like members may be provided, one of them inverted, each member having its associated transmitter/receiver pair. In stable conditions, the oscillation frequencies of the pairs will be equal, and changes in humidity or ambient temperature will affect both frequencies substantially equally so that such changes can be ignored. However, the introduction of a heavy gas or a light gas into the atmosphere would change the frequency of the relevant one of the transmitter/receiver pairs, and a warning would be initiated. The system therefore provides some differentiation between normal changes and potentially dangerous changes in the atmosphere.

A particular application of such a system is the detection of a leak in a pipeline, such as the floating hose connected to a marine tank for filling or unloading purposes. The trough-like members would be positioned above and below the hose so that they cover the extent of the hose. Normally there should be no pollution of the atmosphere surrounding the pipeline, and both frequencies should therefore be the same. Any changes in both frequencies in the same sense would be due to changes in the ambient temperature, and such changes could be compared with the weather conditions and a check on the operation of the system would therefore be achieved (i.e. the frequency changes should correspond to the weather changes). However, if a leak occurs in the pipe, the escaping vapour will affect the frequency of one of the transmitter/receiver pairs. This can, again, be compared with the results expected from a knowledge of the fluid concerned and the ambient temperature, thereby giving a further check on the correctness of the monitoring.

In the above descriptions it has been assumed that the ultrasonic waves follow straight line paths in the air, but the waves can be made to follow curved paths if so required. This feature can be applied, for example, to the checking of a cylindrical or spherical tank or process vessel. Referring to FIG. 5, a tank 50 has as skirt 52 facing upwards around its base. The transmitter 2 and the receiver 4 are positioned back-to-back within the skirt 52 so that the waves from the transmitter 2 are contained within the skirt and travel round the periphery of the tank to reach the receiver 4. The transmitter 2 and the receiver 4 are connected in a phased-locked loop as in FIG. 1. This arrangement warns against leakage of heavy gases from the tank. It may be necessary to provide more than one transmitter/receiver pair round the periphery of the tank, so that the length of the wave path is shortened.

Alternatively, or additionally, an inverted troughlike skirt 54 can be positioned round the top of the tank 50, with one/or more transmitter/receiver pairs positioned therein to warn against the leakage of light gases from the tank.

In some circumstances the material leaking from the tank will be in liquid form, in which case droplets fall into the skirt 52. This occurrence will be shown by the monitor as a sudden change due to temporary interruption of the ultrasonic waves by the liquid, followed by a change in frequency as the droplets vaporise. Since the rate of vaporisation depends upon the nature of the liquid, it is possible to distinguish which of a number of liquids, e.g. water, gasoline and fuel oil, has leaked.

An alternative apparatus, which can be used in place of the apparatus of FIG. 1, is shown in FIG. 6 of the drawings. In FIG. 6, components having the same function as in FIG. 1 have the same reference numerals as in that figure.

This embodiment does not have the phase-locked loop of FIG. 1, but instead includes a phase comparator 56 which compares the modulation phase at the receiver with that at the transmitter 2. The modulation frequency is maintained constant by a signal applied to the voltage controlled oscillator 6 by a control unit 58.

Changes in gas content in the space between the transmitter 2 and the receiver 4 will give rise to a change in the modulation phase at the receiver 4 as compared with that at the transmitter 2, and the phase comparator 56 will provide an output on a line 60 indicative of the gas content. This signal can be fed to the line 28 in FIG. 2, in place of the signal from the line 14 of FIG. 1. Clearly, suitable circuitry must be provided in the central processor 34 for processing the signal.

In any of the above embodiments, the initiation of an alarm by the monitoring apparatus can, if required, be made to cause automatic operation of any of a number of preventive devices. For example, various types of valves could be automatically opened to release foam or water or other fire extinguishants. The releasing of the extinguishants, or of a steam curtain, could itself be monitored by the apparatus, since the molecular weight of the extinguishant or steam varies considerably from that of air, and a large change in modulation frequency would result.

The logic in the processor may be made to distinguish between the presence of steam and the presence of a gas in the monitored atmosphere.

The monitoring apparatus in accordance with the invention will have many other possible applications. For example, the build-up of gases in effluent ducts, pipes or sewers could be monitored.

Since the transmitter/receiver loops can be operated singly, even over a large installation, the power consumption of the monitoring apparatus on the site can be quite small, and the whole installation can be intrinsically safe. In fact, the installation could be run from a sealed battery which is trickle-charged by solar cells; a considerable advantage on sites where power supplies are limited.

In using frequency modulation of the ultrasonic waves to provide gas detection, the present invention provides a number of advantages. The use of unmodulated signals would be possible, but reflections can occur so that it is not clear whether the correct mode is being monitored.

The low frequency modulation effectively makes the monitored wavelength much greater and therefore facilitates monitoring and/or correction of any phase displacement between the transmitted and received waves.

In the phase-locked loop circuit, the type of detector used for detecting frequency modulation is such that only the largest signals are detected, and all spurious signals are rejected.

The carrier frequency should be made as high as possible consistent with the length of the wave path between the transmitting and receiving transducers. The higher the carrier frequency, the more concentrated will be the ultrasonic beam and the greater the sensitivity. On the other hand, the higher the frequency the greater will be the attenuation over a given path length. A compromise must be achieved between these conflicting factors. In general, it is found that a carrier frequency around 30kHz is satisfactory for path lengths up to 20 meters, whilst the frequency may be as high as 2 MHz or more for path lengths of around 1 cm.

The audio modulation frequency is chosen according to the sensitivity required of the apparatus and upon the path length. The wavelength of the modulation should be a fraction of the path length to allow for readily detectable changes in the modulation frequency. For a path length of up to 5 meters, modulation frequency of 1 kHz is convenient.

I claim:

1. An alarm system for providing an alarm when an undesirable gas content occurs in the free atmosphere on a site, the system comprising:
   means to generate a carrier electric signal;
   an audio frequency signal generator;
   a frequency modulator coupled to the carrier signal generator and to the audio frequency generator and operative to frequency modulate the carrier signal with the audio frequency signal;
   a first transducer energisable by the frequency-modulated carrier signal to transmit modulated ultrasonic energy into said free atmosphere;
   means responsive to the relationship between the phase of the audio modulation of the ultrasonic energy received by a second transducer and the phase of the audio modulation of the ultrasonic energy transmitted by the first transducer to generate a signal dependent upon said gas content; and
   means coupled to the phase relationship responsive means to generate an alarm signal in response to the occurrence of a said undesirable gas content.

2. Apparatus as claimed in claim 1, including a display coupled to said alarm signal generating means to indicate the position of detection of said undesirable gas content.

3. Apparatus as claimed in claim 2, wherein said display is remote from said alarm signal generating means and is coupled thereto by a radio link.

4. Apparatus as claimed in claim 2, including means to maintain the audio modulation frequency constant so that the phase relationship of the modulation varies with the gas content.

5. Apparatus as claimed in claim 2, wherein the phase relationship responsive means includes means to maintain the modulation phase relation constant so that the audio modulation frequency varies with the gas content.

6. Apparatus as claimed in claim 5, wherein said modulation audio frequency signal generator is connected in a phaselocked loop including said transducers.

7. Apparatus as claimed in claim 6, wherein said modulation audio frequency signal generator comprises a voltage-controlled oscillator which is controlled by the output of said second transducer.

8. Apparatus as claimed in claim 1, including trough-like means extending between the transducers to collect in the path of the ultrasonic energy heavy gases present in the atmosphere.

9. Apparatus as claimed in claim 1, including trough-like means mounted open-side downwards and extending between the transducers to collect in the path of the ultrasonic energy light gases present in the atmosphere.

10. Apparatus as claimed in claim 1, wherein said transducers are encapsulated in a resin material.

11. An alarm system for warning of the presence of an undesirable gas content in the atmosphere on a site, the system comprising: a plurality of pairs of transducers spaced apart over the site so that each pair monitors a respective region of the site; means to feed an electrical signal which is frequency modulated at an audio frequency to one transducer of each of said pairs so that each said transducer transmits frequency modulated ultrasonic energy to the other transducer of the pair; means responsive to the phase relationship between the audio frequency modulation received by said other transducer and the transmitted audio frequency modulation to monitor the gas content in the respective region and to generate an alarm signal in response to the detection thereby of an undesirable gas content; and a display comprising respective indicating means for each transducer pair to indicate the position of said undesirable gas content.

12. A system as claimed in claim 11, wherein said display is remote from the site and is coupled to the alarm signal generating means by a radio link.

13. A system as claimed in claim 11, including means to cause monitoring operation by said pairs of transducers in sequence.

14. A system as claimed in claim 11, including data processing means to store data representing acceptable events and to nullify any alarm signal which would result from an acceptable event.

15. A system as claimed in claim 11, including at least one battery for energizing the apparatus; and solar cell means for charging the or each battery.

* * * * *

UNITED STATES PATENT OFFICE
CERTIFICATE OF CORRECTION

PATENT NO. : 4,119,950
DATED : October 10, 1978
INVENTOR(S) : Robert J. Redding

It is certified that error appears in the above-identified patent and that said Letters Patent are hereby corrected as shown below:

Column 7, after "atmosphere;", line 62, insert the following paragraph:

--a second transducer spaced from the first transducer across the site for receiving at least part of the modulated ultrasonic energy transmitted through said free atmosphere;--

Signed and Sealed this

Third Day of April 1979

[SEAL]

Attest:

RUTH C. MASON
Attesting Officer

DONALD W. BANNER
Commissioner of Patents and Trademarks